US008821839B2

(12) United States Patent
Carnali et al.

(10) Patent No.: US 8,821,839 B2
(45) Date of Patent: Sep. 2, 2014

(54) COMPOSITIONS AND METHODS FOR IMPARTING A SUNLESS TAN WITH A VICINAL DIAMINE

(75) Inventors: Joseph Oreste Carnali, Newton, CT (US); Qiang Qiu, Ridgewood Cottage (CN)

(73) Assignee: Conopco, Inc., Englewood Cliffs, NJ (US)

( * ) Notice: Subject to any disclaimer, the term of this patent is extended or adjusted under 35 U.S.C. 154(b) by 259 days.

(21) Appl. No.: 12/909,874

(22) Filed: Oct. 22, 2010

(65) Prior Publication Data

US 2012/0100083 A1    Apr. 26, 2012

(51) Int. Cl.
*A61K 8/00*    (2006.01)
*A61K 8/18*    (2006.01)
*A61Q 17/04*    (2006.01)
*A61Q 1/02*    (2006.01)
*A61Q 19/04*    (2006.01)
*A61K 8/41*    (2006.01)

(52) U.S. Cl.
CPC .. *A61Q 19/04* (2013.01); *A61K 8/41* (2013.01)
USPC .............................................. 424/59; 424/63

(58) Field of Classification Search
USPC ...................................................... 424/59, 63
See application file for complete search history.

(56) References Cited

U.S. PATENT DOCUMENTS

| | | |
|---|---|---|
| 3,892,881 A | 7/1975 | Lissant |
| 4,104,403 A | 8/1978 | Barker |
| 4,246,285 A | 1/1981 | Van Duzee |
| 4,385,049 A | 5/1983 | Cuca |
| 4,405,616 A | 9/1983 | Rajadhyaksha ............... 424/244 |
| 4,446,051 A | 5/1984 | Berthod et al. |
| 4,606,913 A | 8/1986 | Aronson |
| 4,808,610 A | 2/1989 | Munayyer et al. |
| 4,886,783 A | 12/1989 | Minaskanian et al. .......... 574/29 |
| 4,981,845 A | 1/1991 | Pereira |
| 5,118,845 A | 6/1992 | Peck et al. ..................... 564/215 |
| 5,131,911 A | 7/1992 | Lang et al. |
| 5,232,688 A | 8/1993 | Ziegler et al. ................... 424/59 |
| 5,387,417 A | 2/1995 | Rentsch |
| 5,412,004 A | 5/1995 | Tachibana et al. |
| 5,489,429 A | 2/1996 | Griat et al. |
| 5,523,075 A | 6/1996 | Fuerst et al. |
| 5,612,044 A | 3/1997 | Suares et al. ................... 424/401 |
| 5,645,822 A | 7/1997 | Meyer et al. ..................... 424/59 |
| 5,700,452 A | 12/1997 | Deckner et al. |
| 5,705,145 A | 1/1998 | Miklean et al. |
| 5,720,948 A | 2/1998 | Brucks et al. ............... 424/78.02 |
| 5,750,092 A | 5/1998 | Meyer et al. ..................... 424/59 |
| 5,756,075 A | 5/1998 | Meyer ............................. 424/59 |
| 5,814,659 A | 9/1998 | Elden |
| 5,827,506 A | 10/1998 | McShane et al. |
| 5,833,973 A | 11/1998 | Dobkowski |
| 5,908,707 A | 6/1999 | Cabell |
| 5,977,194 A | 11/1999 | Mork |
| 6,033,648 A | 3/2000 | Candau |
| 6,060,041 A | 5/2000 | Candau et al. |
| 6,069,169 A | 5/2000 | Ptchelintsev et al. |
| 6,147,131 A | 11/2000 | Mork |
| 6,231,837 B1 | 5/2001 | Stroud et al. ..................... 424/59 |
| 6,303,834 B1 | 10/2001 | Mork |
| 6,313,181 B1 | 11/2001 | Cohen |
| 6,326,033 B1 | 12/2001 | Darmenton et al. |
| 6,352,701 B1 | 3/2002 | Scholz et al. |
| 6,383,503 B1 | 5/2002 | Bleckmann |
| 6,399,046 B1 | 6/2002 | Schonrock et al. |
| 6,423,326 B1 | 7/2002 | Shapiro |
| 6,475,500 B2 | 11/2002 | Vatter |
| 6,524,598 B2 | 2/2003 | Sunkel |
| 6,548,050 B1 | 4/2003 | Bara |
| 6,645,474 B1 | 11/2003 | Galdi et al. |
| 6,685,952 B1 | 2/2004 | Ma et al. |
| 6,696,049 B2 | 2/2004 | Vatter |
| 6,699,488 B2 | 3/2004 | Deckner |
| 6,747,115 B2 | 6/2004 | Sakuta |
| 6,793,929 B2 | 9/2004 | Bleckmann |
| 7,166,276 B2 | 1/2007 | Stephens et al. |
| 7,175,835 B1 | 2/2007 | Simoulidis et al. |
| 7,316,808 B2 | 1/2008 | Candau |
| 7,416,735 B2 | 8/2008 | El-Nokaly et al. |
| 7,462,363 B2 | 12/2008 | Braun |
| 7,807,188 B2 | 10/2010 | Hoath et al. |
| 8,241,614 B2 | 8/2012 | Carnali |
| 8,299,127 B2 | 10/2012 | Anjing |
| 8,398,959 B2 | 3/2013 | Yang et al. |

(Continued)

FOREIGN PATENT DOCUMENTS

CN        1816316 A        8/2006
CN        101068528 A      5/2011

(Continued)

OTHER PUBLICATIONS

GB Search Report on Application No. GB1116661.8 dated Jan. 16, 2012.
Co-pending Application: Applicant: Carnali; U.S. Appl. No. 12/627,566, filed Nov. 30, 2009.
Co-pending Application: Applicant: Lou et al., U.S. Appl. No. 12/855,348, filed Aug. 21, 2010.
Co-pending Application: Applicant: Lou; U.S. Appl. No. 12/784,046, filed May 20, 2010.
Wikipedia, "Microemulsion"—Retrieved online Feb. 7, 2014—4 pages.
Carbopol® Aqua SF-1 Polymer, Lubrizol Technical Data Sheet, Feb. 7, 2013, pp. 1-9.

(Continued)

*Primary Examiner* — Gina C Justice
*Assistant Examiner* — Genevieve S Alley
(74) *Attorney, Agent, or Firm* — Edward A. Squillante, Jr.

(57) ABSTRACT

A composition and method for imparting a sunless tan to skin is described. The composition and method makes use of a sunless tanning agent like dihydroxyacetone in combination with an adjuvant which is a vicinal diamine.

12 Claims, No Drawings

(56) References Cited

U.S. PATENT DOCUMENTS

| | | |
|---|---|---|
| 8,425,882 B2 | 4/2013 | Lou et al. |
| 2002/0028184 A1 | 3/2002 | Sunkel |
| 2002/0028223 A1 | 3/2002 | Vatter et al. |
| 2002/0051755 A1 | 5/2002 | Candau et al. |
| 2002/0106385 A1 | 8/2002 | Vatter |
| 2002/0142018 A1 | 10/2002 | Scholz et al. |
| 2003/0021815 A9 | 1/2003 | Mondet |
| 2003/0044365 A1 | 3/2003 | Candau |
| 2003/0049212 A1 | 3/2003 | Robinson et al. |
| 2003/0082119 A1 | 5/2003 | Golz-Berner et al. |
| 2003/0108498 A1 | 6/2003 | Stephens et al. |
| 2003/0170193 A1 | 9/2003 | Pate |
| 2003/0211061 A1 | 11/2003 | Deckner |
| 2003/0211069 A1 | 11/2003 | Deckner |
| 2003/0228339 A1 | 12/2003 | El-Nokaly et al. |
| 2004/0014653 A1 | 1/2004 | Smith |
| 2004/0047819 A1 | 3/2004 | Hansenne et al. |
| 2004/0076597 A1 | 4/2004 | Berens et al. |
| 2004/0086474 A1 | 5/2004 | Rabe et al. |
| 2004/0091437 A1 | 5/2004 | Fack et al. |
| 2004/0146472 A1 | 7/2004 | Nakanishi |
| 2004/0185072 A1 | 9/2004 | Hitzel et al. |
| 2004/0208903 A1 | 10/2004 | Robinson et al. |
| 2004/0228821 A1 | 11/2004 | Sunkel et al. |
| 2004/0235693 A1 | 11/2004 | Wei |
| 2005/0002978 A1 | 1/2005 | Crook et al. |
| 2005/0008600 A1 | 1/2005 | Nakanishi |
| 2005/0089486 A1 | 4/2005 | Spindler et al. ............... 424/59 |
| 2005/0118218 A1 | 6/2005 | Cassin |
| 2005/0163812 A1 | 7/2005 | Hoath et al. |
| 2005/0169856 A1 | 8/2005 | Grollier |
| 2005/0175570 A1 | 8/2005 | Inoue |
| 2005/0191326 A1 | 9/2005 | Melker |
| 2005/0238595 A1 | 10/2005 | Stella |
| 2006/0008426 A1 | 1/2006 | Doring et al. |
| 2006/0013790 A1 | 1/2006 | Shimizu |
| 2006/0078524 A1 | 4/2006 | Midha |
| 2006/0078527 A1 | 4/2006 | Midha et al. |
| 2006/0079417 A1 | 4/2006 | Wagner et al. |
| 2006/0079422 A1 | 4/2006 | Midha |
| 2006/0127344 A1 | 6/2006 | Zofchak |
| 2006/0171909 A1 | 8/2006 | Morrissey et al. |
| 2007/0009463 A1 | 1/2007 | NiebaueR |
| 2007/0020217 A1 | 1/2007 | Themens |
| 2007/0067924 A1 | 3/2007 | Beck et al. |
| 2007/0173599 A1 | 7/2007 | Liu |
| 2007/0231355 A1 | 10/2007 | Quadir et al. |
| 2007/0292373 A1 | 12/2007 | Russ et al. |
| 2008/0081057 A1 | 4/2008 | Chevalier |
| 2008/0279793 A1 | 11/2008 | Rudolph et al. |
| 2008/0279796 A1 | 11/2008 | Handrosch et al. |
| 2008/0299058 A1 | 12/2008 | Saito |
| 2008/0299156 A1 | 12/2008 | Fares |
| 2008/0311058 A1 | 12/2008 | Lou |
| 2008/0317693 A1 | 12/2008 | Ricard |
| 2009/0035241 A1 | 2/2009 | Cassin et al. |
| 2009/0041688 A1 | 2/2009 | Dueva-Koganov et al. |
| 2009/0155321 A1 | 6/2009 | Harichian et al. ............ 424/401 |
| 2009/0155322 A1 | 6/2009 | Harichian et al. |
| 2009/0155373 A1 | 6/2009 | Huang et al. |
| 2009/0178209 A1 | 7/2009 | Koike et al. |
| 2009/0247445 A1 | 10/2009 | Lou |
| 2009/0280147 A1 | 11/2009 | Alberius et al. |
| 2010/0035783 A1 | 2/2010 | Restrepo et al. |
| 2010/0209364 A1 | 8/2010 | Abe et al. |
| 2010/0310483 A1 | 12/2010 | Klug et al. |
| 2011/0150802 A1 | 6/2011 | Bui et al. |
| 2011/0150805 A1 | 6/2011 | Kergosien et al. |
| 2011/0150807 A1 | 6/2011 | Bui et al. |
| 2011/0286942 A1 | 11/2011 | Lou |
| 2011/0305649 A1 | 12/2011 | Lou |
| 2011/0305651 A1 | 12/2011 | Carnali |
| 2012/0039967 A1 | 2/2012 | Lou et al. |
| 2012/0100083 A1 | 4/2012 | Carnali |
| 2012/0141393 A1 | 6/2012 | Yang |
| 2012/0189676 A1 | 7/2012 | Susak et al. |

FOREIGN PATENT DOCUMENTS

| | | |
|---|---|---|
| DE | 4122033 A1 | 1/1993 |
| DE | 10049041 A1 | 4/2002 |
| DE | 102004055541 A1 | 5/2006 |
| DE | 102007013368 A1 | 9/2008 |
| DE | 102008006857 A1 | 1/2009 |
| EP | 1465530 | 2/1974 |
| EP | 0009404 B1 | 2/1984 |
| EP | 0160430 A2 | 11/1985 |
| EP | 0302147 A1 | 2/1989 |
| EP | 0456545 A1 | 11/1991 |
| EP | 0500446 A1 | 8/1992 |
| EP | 810181 A2 | 12/1997 |
| EP | 1210933 A1 | 6/2002 |
| EP | 1352639 A1 | 10/2003 |
| EP | 1481660 | 12/2004 |
| EP | 1581660 A1 | 12/2004 |
| EP | 1600144 A1 | 11/2005 |
| EP | 1741422 A1 | 1/2007 |
| EP | 1849498 A2 | 10/2007 |
| EP | 2087879 A1 | 8/2009 |
| EP | 2380557 A1 | 10/2011 |
| EP | 1864647 B1 | 11/2011 |
| FR | 2651126 A1 | 3/1991 |
| FR | 2894468 A1 | 12/2005 |
| GB | 1465528 | 2/1977 |
| GB | 1465529 | 2/1977 |
| GB | 2139919 A | 11/1984 |
| JP | 57091733 | 6/1982 |
| JP | 1281140 A | 11/1989 |
| JP | 11158032 | 6/1999 |
| JP | 2004107249 A | 4/2004 |
| JP | 2005314327 A | 11/2005 |
| WO | WO9217159 A2 | 10/1992 |
| WO | WO9403148 A2 | 2/1994 |
| WO | WO9415580 A1 | 7/1994 |
| WO | WO9421221 A1 | 9/1994 |
| WO | WO9526178 A1 | 10/1995 |
| WO | W09621721 A1 | 7/1996 |
| WO | 97/33560 | 9/1997 |
| WO | WO 97/33560 * | 9/1997 |
| WO | WO0100141 A1 | 1/2001 |
| WO | WO0107003 A1 | 2/2001 |
| WO | WO0128552 A2 | 4/2001 |
| WO | WO0189464 A1 | 11/2001 |
| WO | WO03022235 A2 | 3/2003 |
| WO | WO03075879 A2 | 9/2003 |
| WO | WO03080005 A1 | 10/2003 |
| WO | WO03086339 A1 | 10/2003 |
| WO | WO2004105721 A1 | 12/2004 |
| WO | WO2005004833 A1 | 1/2005 |
| WO | WO2005016302 A1 | 2/2005 |
| WO | WO2005025505 A2 | 3/2005 |
| WO | WO2006018149 A1 | 2/2006 |
| WO | WO2006102289 A2 | 9/2006 |
| WO | WO2007064687 A1 | 6/2007 |
| WO | WO 2008/013757 * | 1/2008 |
| WO | WO2008013757 | 1/2008 |
| WO | WO2008018046 A2 | 2/2008 |
| WO | WO2008155228 A2 | 12/2008 |
| WO | WO2009014061 A1 | 1/2009 |
| WO | WO2009053287 A1 | 4/2009 |
| WO | WO2009074513 A1 | 6/2009 |
| WO | WO2009083545 A2 | 7/2009 |
| WO | WO2009121787 A1 | 10/2009 |
| WO | WO2010009989 A1 | 1/2010 |
| WO | WO2010045163 A2 | 4/2010 |
| WO | WO2011075871 A1 | 6/2011 |
| WO | WO2011090821 A1 | 7/2011 |
| WO | WO2011157640 A2 | 12/2011 |

OTHER PUBLICATIONS

Shin-Etsu-Silicone for Personal Care, Shin-Etsu Chemical Co., Ltd., 2004, 1-6.

(56) References Cited

OTHER PUBLICATIONS

Dussaud, Liquid Transport in the Networked Microchannels of the Skin Surface, Langmuir, May 30, 2003, 7341-7345, 19, American Chemical Society, US.

LotionCrafter, Cyclomethicone and Essential Oils, Cyclomethicone and Essential 011s, 1-3, US.

Shin Etsu, Silicone Products for Personal Care-Shin-Etsu Unique Materials, ShinEtsu Silicone, 2007, 1-20.

* cited by examiner

COMPOSITIONS AND METHODS FOR IMPARTING A SUNLESS TAN WITH A VICINAL DIAMINE

FIELD OF THE INVENTION

The present invention is directed to a composition and method for imparting a sunless tan to skin. More particularly, the invention is directed to a composition and method that employ a sunless tanning agent as well as an adjuvant for the sunless tanning agent. The composition, when applied, unexpectedly results in the consumer having skin with a brownish/tan coloration (i.e., a sunless tan) within a consumer acceptable time and in the absence of undesirable orange coloration.

BACKGROUND OF THE INVENTION

Sunless tanning agents are formulated into two types of cosmetic products. Of these, the most traditional is the self-tanning lotion. The imparted benefit is to achieve a skin coloration equivalent to that from basking in the sun. More recently, a second product category has arrived. Therein a sunless tanning agent in small amounts is added to a typical moisturizing lotion. A "glow or shine" is thereby imparted. Glow or shine is a major factor in the appearance of healthy looking skin.

Most prominent among the sunless tanning agents is dihydroxyacetone ("DHA" which is also chemically known as 1,3-dihydroxy-2-propanone). DHA, after application, is believed to exert its effect through interactions between, for example, its keto group and the amino groups of amino acids and peptides naturally occurring in the stratum corneum of the skin. These so-called Maillard reactions are believed (see, e.g., Bobin et al., J. Soc. Cosmet. Chem. 35: 255 (1984)) to lead to formation of brown pigments in the skin, thereby giving it an appearance similar to that of a naturally obtained tan.

Unfortunately, many sunless tanning products available on the market are not stable in that they turn a yellow and/or orange color after application, especially when exposed to UV light. Other sunless tanning products perform poorly and do not quickly impart a noticeable brown color after application. These poorly performing products do not discourage "tan-happy" consumers from basking in the sun. Such behavior then leads to consumers with skin over exposed to the sun's harmful ultraviolet rays.

There is increasing interest to develop compositions and methods for imparting a sunless tan. This invention, therefore, is directed to a composition and method that employ a sunless tanning agent as well as an adjuvant for the sunless tanning agent. The composition, when applied, unexpectedly results in the consumer having skin with a natural brownish/tan coloration within a consumer acceptable time and, surprisingly, does not turn orange and/or yellow after application.

Additional Information

Efforts have been disclosed for making self-tanning cosmetic compositions. In U.S. Pat. Nos. 5,232,688 and 5,612,044, self-tanner compositions with DHA are described.

Other efforts have been disclosed for making self-tanning compositions. In U.S. Pat. No. 5,750,092, compositions with DHA and secondary amines are described.

Still other efforts have been disclosed for making self-tanning compositions. In U.S. Pat. No. 6,231,837, self tanning formulations comprising DHA, polyethoxyglycol and a polyol are described.

Even other efforts have been disclosed for creating sunless tans. In U.S. Pat. Nos. 5,645,822 and 5,756,075, and Published Patent Application No. 2005/0089486, sunless tanning concepts are described.

None of the additional information describes a method and/or composition that yield excellent sunless tanning results whereby the composition and method employ a sunless tanning agent and a vicinal diamine as claimed herein.

SUMMARY OF THE INVENTION

In a first aspect, the present invention is directed to a composition comprising:
a) a sunless tanning agent; and
b) an adjuvant for the sunless tanning agent, the adjuvant comprising a vicinal diamine
wherein at least about 50% by weight of the vicinal diamine is not loaded onto a microparticle delivery system.

In a second aspect, the present invention is directed to a method for generating a sunless tan comprising the step of applying to the skin the composition of the first aspect of this invention.

All other aspects of the present invention will more readily become apparent upon considering the detailed description and examples which follow.

Sunless tanning, as used herein, means obtaining the suntan look by applying a topical composition. The same can be interchanged with self-tanning. Composition, as used herein, is meant to include a substance applied to a human body for imparting a sunless tan where the composition is for example, a leave-on skin lotion, cream or mousse, shampoo, hair conditioner, shower gel, toilet bar, body wash, shaving cream, body wax, depilatory, mascara, sunscreen product or the like. Such a composition may also be put on body towelettes for application to the body. In a preferred embodiment, the composition of this invention is a lotion or cream. Consumer acceptable time means within about 3 to about 6 hours from application, and preferably, from about 1 to about 2 hours, and most preferably, from about 15 to about 30 minutes subsequent to application. Microparticle delivery system, as used herein, is meant to mean a delivery system using adsorbent microparticle polymers like, for example, those sold under the name Poly-Pore® E200 and PolyTrap®, both of which are made commercially available from suppliers like AMCOL International Corp.

Comprising, as used herein, is meant to include consisting essentially of and consisting of. Therefore, for example, the adjuvant used in the present invention may consist essentially of or consist of vicinal diamine. All ranges identified herein are meant to include all ranges subsumed therein if, for example, reference to the same is not explicitly made.

DETAILED DESCRIPTION OF THE INVENTION

The sunless tanning agent suitable for use in this invention is only limited to the extent that the same may be applied topically by humans to form pigmented components. Such materials may be alpha-hydroxyaldelydes and ketones, glyceraldehyde, troxerutin and related alcohol aldehydes, various indoles, imidazoles as well as mixtures and derivatives thereof.

Illustrative yet non-limiting examples of the sunless tanning agents that may be used in this invention include DHA, melanin, mahakanni (eclipta alba), methyl glyoxal, erythrulose, alloxan, 2,3-dihydroxysuccindialdehyde, mixtures thereof, or the like. In a preferred embodiment, the sunless tanning agent used is dihydroxyacetone, erythrulose or a mixture thereof. In a most preferred embodiment, the sunless tanning agent is DHA.

Typically, suitable sunless tanning agent makes up from about 0.025 to about 35%, and preferably, from about 0.05 to about 15%, and most preferably, from about 0.5 to about 10% by weight of the composition (i.e., the composition suitable for topical application by a consumer), based on total weight of the composition and including all ranges subsumed therein.

The adjuvant (i.e., vicinal, primary diamine) that may be used in this invention is limited only to the extent that the same may be used in a composition suitable for topical application to humans.

Typically, suitable vicinal diamine is represented by the formula:

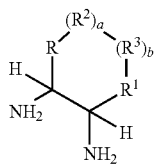

wherein
a and b are each independently zero or 1;
R is H, or $C_{1-4}$ alkyl when a is zero and CH—X when a is 1;
$R^1$ is H or $C_{1-4}$ alkyl when b is zero and CH—X when b is 1;
when a is 1, $R^2$ is H, $C_{1-4}$ alkyl or a $C_{1-3}$ alkoxy when b is zero, and CH—X or Y when b is 1;
when b is 1, $R^3$ is H, $C_{1-4}$ alkyl or a $C_{1-3}$ alkoxy when a is zero, and CH—X or Y when a is 1;
each X is independently H, OH, $C_{1-3}$ alkyl or —$CH_2(CH_2)_n$OH where n is an integer from zero to 2;
Y is oxygen or $NR^4$; and
each $R^4$ is independently H, $C_{1-6}$ alkyl, aryl or —$CH_2$—$(CH_2)_m$—OH where m is an integer from about 0 to about 4.

Included within the scope of this invention are the geometric isomers of the above-identified vicinal diamines.

In an often preferred embodiment, at least about 50%, and preferably, at least about 65%, and most preferably, from 75 to 100% by weight vicinal diamine is not loaded onto a microparticle delivery system. Most preferably, the adjuvant of this invention is added to the composition as an ingredient or additive free of any delivery or additive system.

If optionally used, microparticle delivery system may extend the life of sunless tanning agent and/or assist in suspending non-soluble ingredients within the composition. Such particles may be made by combining from about 1 to about 3 parts by weight adjuvant to about 3 to 1 parts by weight microparticle polymer. Preferred microparticle polymers include PolyPore® E200, Poly-Pore L200 and Poly-Trap®, all of which are made commercially from AMCOL International Corporation. A more detailed description of such a microparticle delivery system is described in U.S. patent Application No. 2005/0089486, the disclosure of which is incorporated herein by reference.

In a preferred embodiment, the adjuvant employed in this invention and represented by the formula is ethylene diamine, 1,2-diamino propane, 1,2-diamino cyclohexane, 3,4-diamino-6-hydroxymethyl-tetrahydro-pyran-2,5-diol, a mixture thereof or the like. In a more preferred embodiment, the adjuvant used is the 1,2-diamino propane, 1,2-diamino cyclohexane or a mixture thereof.

In a most preferred embodiment, the pH of the composition of this invention is from about 2.6 to less than 3.8, and preferably, from about 2.7 to about 3.7, and most preferably, from about 3.0 to about 3.5, including all ranges subsumed therein. In an especially preferred embodiment, the pH of the composition is from about 3.0 to about 3.5 when at least about 50% by weight of total adjuvant and especially all adjuvant used is ethylene diamine.

Typically, adjuvant makes up from about 0.025 to about 35%, and preferably, from about 0.05 to about 15%, and most preferably, from about 0.5% to about 8% by weight of the composition, including all ranges subsumed therein.

Compositions of the present invention will typically include a cosmetically acceptable carrier. Water is the most preferred carrier. Amounts of water may range from about 1 to about 99%, and preferably, from about 5 to about 90%, and most preferably, from about 35 to about 80% and optimally from about 40 to about 75% by weight, based on total weight of the composition and including all ranges subsumed therein. Ordinarily the compositions will be water and oil emulsions, most preferably, of the oil-in-water variety. Water-in-oil emulsions, and especially, those generally classified as water-in-oil and high internal phase emulsions are, however, an option. Illustrative examples of the high internal phase emulsions suitable to carry the actives and adjuvants of this invention described in commonly owned U.S. Patent Application Publication Nos. 2008/0311058 and 2009/0247445, the disclosures of which are incorporated herein by reference.

Other cosmetically acceptable carriers may include mineral oils, silicone oils, synthetic or natural esters, fatty acids and alcohols. Amounts of these materials may range from about 0.1 to about 50%, and preferably, from about 0.1 to about 30%, and most preferably, from about 1 to about 20% by weight of the composition, including all ranges subsumed therein.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, and preferably, from about 4 to about 5 silicon atoms.

Linear volatile silicone materials generally have viscosities less than about 5 centistokes at 25° C. while cyclic materials typically have viscosities of less than about 10 centistokes. Nonvolatile silicone oils useful as carrier material include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from about 5 to about 100,000 centistokes at 25° C.

An often preferred silicone source is a cyclopentasiloxane and dimethiconol solution.

Among suitable esters are:
(1) Alkenyl or alkyl esters of fatty acids having 10 to 20 carbon atoms like isopropyl palmitate, isopropyl isostearate, isononyl isononanoate, oleyl myristate, oleyl stearate, and oleyl oleate;
(2) Ether-esters such as fatty acid esters of ethoxylated fatty alcohols;
(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol monoand di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxy-ethylene sorbitan fatty acid esters;

(4) Wax esters such as beeswax, spermaceti, myristyl myristate, stearyl stearate; and (5) Sterol esters, of which soya sterol and cholesterol fatty acid esters are examples thereof.

Fatty acids having from 10 to 30 carbon atoms may be included in the compositions of this invention. Illustrative of this category are pelargonic, lauric, myristic, palmitic, stearic, isostearic, oleic, linoleic, ricinoleic, arachidic, behenic and erucic acids.

Emulsifiers may be present in the compositions of the present invention. Total concentration of the emulsifier may range from about 0.1 to about 40%, and preferably, from about 1 to about 20%, and most preferably, from about 1 to about 5% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Preservatives can desirably be incorporated into the compositions comprising the sunless tanning agent and adjuvant of this invention to protect against the growth of potentially harmful microorganisms. Suitable traditional preservatives for compositions of this invention are alkyl esters of parahydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition, including all ranges subsumed therein.

Thickening agents may be included in compositions of the present invention. Particularly useful are the polysaccharides. Examples include starches, natural/synthetic gums and cellulosics. Representative of the starches are chemically modified starches such as sodium hydroxypropyl starch phosphate. Tapioca starch is an often desired option. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, and ethylcellulose.

Amounts of the thickener may range from about 0.001 to about 5%, and preferably, from about 0.1 to about 2%, and most preferably, from about 0.2 to about 0.5% by weight of the composition including all ranges subsumed therein.

Fragrances, fixatives and abrasives may optionally be included in compositions of the present invention. Each of these substances may range from about 0.05 to about 5%, preferably between 0.1 and 3% by weight.

To enhance skin moisturization, cationic ammonium compounds may optionally be used in the compositions of this invention. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the composition.

When cationic ammonium compounds are used, optional additives for use with the same are moisturizing agents such as substituted ureas like hydroxymethyl urea, hydroxyethyl urea, hydroxypropyl urea; bis(hydroxymethyl)urea; bis(hydroxyethyl)urea; bis(hydroxypropyl)urea; N,N'-dihydroxymethyl urea; N,N'-di-hydroxyethyl urea; N,N'-di-hydroxypropyl urea; N,N,N'-tri-hydroxyethyl urea; tetra (hydroxymethyl)urea; tetra(hydroxyethyl)urea; tetra(hydroxypropyl)urea; N-methyl-N'-hydroxyethyl urea; N-ethyl-N'-hydroxyethyl urea; N-hydroxypropyl-N'-hydroxyethyl urea and N,N'dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance. Such substituted ureas, while desirable in moisturizing formulations, are only selected for use when compatible with the desired sunless tanning agent or agents used in the compositions of this invention.

Amounts of substituted urea, when used, in the composition of this invention range from about 0.01 to about 20%, and preferably, from about 0.5 to about 15%, and most preferably, from about 2 to about 10% based on total weight of the composition and including all ranges subsumed therein.

When cationic ammonium compound and substituted urea are used, in a most especially preferred embodiment at least from about 0.01 to about 25%, and preferably, from about 0.2 to about 20%, and most preferably, from about 1 to about 15% humectant, like glycerine, is used, based on total weight of the composition and including all ranges subsumed therein.

In the absence of cationic ammonium compound and substituted urea, conventional humectants may, nevertheless, be employed in the present invention. These are generally polyhydric alcohol-type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed in the absence of cationic ammonium compound and substituted urea may range anywhere from 0.5 to 30%, preferably between 1 and 15% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the end use composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary.

Also optionally suitable for use include materials like lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Conventional buffers/pH modifiers may be used. These include commonly employed additives like sodium hydroxide, hydrochloric acid, citric acid and citrate/citric acid buffers.

Colorants, opacifiers, chelators (like tetrasodium EDTA) and abrasives may also be included in the compositions of the present invention. Each of these substances may range from about 0.05 to about 5%, preferably between 0.1 and 3% by weight of the composition.

In an especially preferred embodiment, the composition of the present invention comprises less than about 5%, and preferably, from 0.01 to 4% glycine, and most preferably, no glycine.

A wide variety of packaging can be employed to store and deliver the compositions. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

Preferably, the composition of this invention may be divided so that a first portion carries sunless tanning agent and a second portion may carry adjuvant. When dividing the composition, each portion should be packaged separately from each other and not come into contact with each other until application to the body. The packaging for dual compositions is known and commercially available. Upon application, the make up of the composition (i.e., the combined portions) is as described herein.

When making the composition of the present invention, ingredients may be combined in no particular order. Typically the ingredients are combined and mixed under conditions of moderate shear and at ambient temperature with pressure being atmospheric conditions. In a most preferred embodiment, DHA and adjuvant are not added at a time when mixing and heating are desired and at a point where their concentrations would be high with respect to each other. When applied by the consumer, typically from about 1 to 5 mg, and preferably, from about 1 to 4 mg, and preferably, from about 1.5 to 2.5 mg per square centimeter of composition is applied to body surface (like skin) and including all ranges subsumed therein.

The following examples are provided to facilitate an understanding of the present invention. The examples are not intended to limit the scope of the claims.

Example 1

The utility of the inventive adjuvants in sunless-tanning compositions is illustrated in the following samples shown in Table I, all of which were made by mixing ingredients with moderate shear under atmospheric conditions and ambient temperature.

TABLE I

| Ingredient | Sample (% by weight) | | |
| --- | --- | --- | --- |
| | E1 | E2 | E3 |
| Sodium hydroxypropyl starch phosphate | 0.10 | 0.10 | 0.10 |
| Chelator | 0.11 | 0.11 | 0.11 |
| Preservative | 0.3 | 0.3 | 0.3 |
| Glycerin | 12.0 | 12.0 | 12.0 |
| Citric acid* | 0.1-0.2 | 0.1-0.2 | 0.1-0.2 |
| Colorant | 0.19 | 0.19 | 0.19 |
| Stearic acid | 1.97 | 1.97 | 1.97 |
| Emulsifier | 4.2 | 4.2 | 4.2 |
| Cetyl alcohol | 0.31 | 0.31 | 0.31 |
| Isopropyl palmitate | 2.25 | 2.25 | 2.25 |
| Silicone oil | 1.5 | 1.5 | 1.5 |
| Phenoxyethanol | 0.4 | 0.4 | 0.4 |
| Fragrance | 0.35 | 0.35 | 0.35 |
| Dihydroxyacetone | 2.5 | 0.0 | 0.0 |
| Alloxan | 0.0 | 2.5 | 0.0 |
| Erythrulose | 0.0 | 0.0 | 2.5 |

TABLE I-continued

| Ingredient | Sample (% by weight) | | |
|---|---|---|---|
| | E1 | E2 | E3 |
| 1,2-Diamino cyclohexane | 1.0 | 1.0 | 1.0 |
| Deionized water | balance | balance | balance |

*to pH of about 3.3

Samples E1 to E3 were assessed for efficacy and all gave coloration to synthetic skin (made available under the Vitro-Skin® name). The synthetic skin was pre-hydrated at 95% RH for 24 hours and then treated with portions of the samples at a dosage of 5 µL/cm². The treated synthetic skin was then stored at 35° C. and 40% RH for periods up to 24 hours. Color development was monitored after about three (3) hours of treatment using a HunterLab Labscan XE colorimeter. The overall color of the treated skin was noted in terms of the Individual Typologic Angle ITA°=180 (Arc Tangent ((L*−50/b*))/π, as defined by A. Chardon et al. in the International Journal of Cosmetic Science, Volume 13, pages 191-208 (1991). When comparing skin treated with compositions having no adjuvant, samples (E1-E3) made according to this invention resulted in skin showing a large difference in ITA° (i.e., ΔITA° of about 40) indicating a darker tan/color. The results demonstrated that the inventive adjuvants of this invention work well across a broad range of sunless tanning actives and in compositions ready for use by consumers.

Example 2

The utility of the inventive ingredients in sunless-tanning compositions was also illustrated in the following samples shown in Table II, all of which were prepared as described above.

TABLE II

| Ingredients | Sample (% by weight) | | |
|---|---|---|---|
| | E4 | E5 | E6 |
| Thickening agent | 0.25 | 0.25 | 0.25 |
| Tapioca starch | 0.5 | 0.5 | 0.5 |
| Chelator | 0.05 | 0.05 | 0.05 |
| Preservative | 0.3 | 0.3 | 0.3 |
| Glycerin | 12.0 | 12.0 | 12.0 |
| Citric acid* | 0.02 | 0.02 | 0.02 |
| Colorant | 0.19 | 0.19 | 0.19 |
| Glyceryl stearate | 2.4 | 2.4 | 2.4 |
| PEG 100 stearate | 1.2 | 1.2 | 1.2 |
| Cetyl alcohol | 2.4 | 2.4 | 2.4 |
| Isopropyl palmitate | 2.0 | 2.0 | 2.0 |
| Wax | 1.0 | 1.0 | 1.0 |
| Dimethicone 50 cst | 3.0 | 3.0 | 3.0 |
| Phenoxyethanol | 0.4 | 0.4 | 0.4 |
| Fragrance | 0.35 | 0.35 | 0.35 |
| Dihydroxyacetone | 2.5 | 0.0 | 0.0 |
| Alloxan | 0.0 | 2.5 | 0.0 |
| Erythrulose | 0.0 | 0.0 | 2.5 |
| Ethylene diamine | 1.0 | 1.0 | 1.0 |
| Deionized water | to 100 | to 100 | to 100 |

*to pH of about 3.3

To assess the effect of the adjuvants of this invention on coloration, a change in the Individual Typological Angle, with and without adjuvant, was determined as a function of time using synthetic skin and in a manner similar to the one described in Example 1. The large values of ΔITA° signify darker tanning or coloring.

The change in the Individual Typologic Angle)(ITA° for synthetic skin 3 hours after treatment with a variety of sunless tanning agents and adjuvant consistent with this invention is shown in Table III.

TABLE III

| Sample | Δ ITA ° for ethylene diamine vs. no adjuvant |
|---|---|
| E4 | 42 |
| E5 | 37 |
| E6 | 38 |

The results in Table III indicate that adjuvant consistent with this invention unexpectedly enhances coloration within a ready to use composition.

Example 3

Formulations in Table IV containing 2.5% DHA and the molar equivalent of 1% glycine as adjuvant in a citric acid/citrate buffer solution were prepared. The formulations were adjusted to a pH of about 5.5 to mimic the formulation pH after application to human skin.

TABLE IV

| Adjuvant | ΔITA ° after 2 hours | ΔITA ° after 4 hours |
|---|---|---|
| None | 0.5 ± 0.5 | 0.5 ± 0.5 |
| Glycine | 2 ± 1 | 7 ± 2 |
| 1,2-diamino cyclohexane | 20 ± 3 | 35 ± 3 |
| Ethylene diamine | 16 ± 2 | 32 ± 3 |
| 1,2-diamino propane | 17 ± 2 | 32 ± 3 |
| 3,4-diamino-6-hydroxymethyl-tetrahydro-pyrane 2,5-diol | 15 ± 3 | 23 ± 2 |
| 1,3-diamino propane | 6 ± 3 | 16 ± 4 |
| 1,4-diamino butane | 4 ± 2 | 12 ± 4 |
| N,N-dimethyl ethylene diamine | 4 ± 2 | 8 ± 2 |

Individual Typologic Angle results were obtained in a manner similar to the one described in Example 1. The results unexpectedly demonstrate that adjuvants of this invention and having adjacent (vicinal) amines resulted in greater skin darkening when compared to non-vicinal diamines such as 1,3-diamino propane, 1,4-diamino propane and non-primary diamines like N,N-dimethyl ethylene diamine.

What is claimed:
1. A composition comprising:
a) a sunless tanning agent; and
b) an adjuvant for the sunless tanning agent, the adjuvant comprising a vicinal primary diamine having the formula

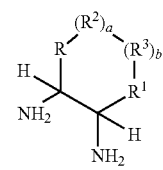

wherein
a and b are each independently zero or 1;
R is H, or $C_{1-4}$ alkyl when a is zero and CH—X when a is 1;

$R^1$ is H or $C_{1-4}$ alkyl when b is zero and CH—X when b is 1;

when a is 1, $R^2$ is H, $C_{1-4}$ alkyl or a $C_{1-3}$ alkoxy when b is zero, and CH—X or Y when b is 1;

when b is 1, $R^3$ is H, $C_{1-4}$ alkyl or a $C_{1-3}$ alkoxy when a is zero, and CH—X or Y when a is 1;

each X is independently H, OH, $C_{1-3}$ alkyl or —$CH_2(CH_2)_n$OH where n is an integer from zero to 2;

Y is oxygen or $NR^4$; and each $R^4$ is independently H, $C_{1-6}$ alkyl, aryl or —$CH_2$—$(CH_2)_m$—OH where m is an integer from about 0 to about 4;

wherein at least about 50% by weight of the vicinal diamine present is not loaded onto a microparticle delivery system, wherein the vicinal diamine comprises 1,2-diamino cyclohexane, and wherein the adjuvant further comprises Vitamin E and/or a derivative thereof.

2. The composition according to claim 1 wherein the sunless tanning agent is dihydroxyacetone, melanin, mehakanni, methyl glyoxal, erythrulose, alloxan, 2,3-dihydroxysuccindialdehyde or a mixture thereof.

3. The composition according to claim 1 wherein the sunless tanning agent is dihydroxyacetone.

4. The composition according to claim 1 wherein from about 75 to 100 percent by weight adjuvant is not loaded onto a microparticle delivery system.

5. The composition according to claim 1 wherein the vicinal primary diamine is 1,2-diamino cyclohexane.

6. The composition according to claim 1 wherein the vicinal primary amine further comprises ethylene diamine, 1,2-diamino propane, 3,4-diamino-6-hydroxymethyl-tetrahydropyran-2,5-diol or a mixture thereof.

7. The composition according to claim 1 wherein the adjuvant further comprises ethylene diamine.

8. The composition according to claim 1 wherein the adjuvant makes up from about 0.025 to about 35% by weight of the composition.

9. The composition according to claim 1 wherein the composition has a pH from about 2.6 to less than 3.8.

10. The composition according to claim 7 wherein the composition has a pH from about 3 to about 3.5.

11. The composition according to claim 1 wherein the sunless tanning agent makes up from about 0.025 to about 35% by weight of the composition.

12. A method for imparting a sunless tan to skin comprising the step of applying to the skin the composition of claim 1.

* * * * *